(12) United States Patent
Ho

(10) Patent No.: US 8,383,873 B2
(45) Date of Patent: Feb. 26, 2013

(54) TERMINAL 1,1-DISUBSTITUTED ALKENES, METHOD OF MAKING AND USING THEREOF

(75) Inventor: Chun Yu Ho, Laguna (CN)

(73) Assignee: The Chinese University of Hong Kong, Hong Kong (CN)

( * ) Notice: Subject to any disclaimer, the term of this patent is extended or adjusted under 35 U.S.C. 154(b) by 385 days.

(21) Appl. No.: 12/706,458

(22) Filed: Feb. 16, 2010

(65) Prior Publication Data

US 2011/0201840 A1  Aug. 18, 2011

(51) Int. Cl.
*C07C 2/24* (2006.01)
(52) U.S. Cl. ........................................ 585/513
(58) Field of Classification Search .................. None
See application file for complete search history.

(56) References Cited

U.S. PATENT DOCUMENTS

| 5,087,788 | A | * | 2/1992 | Wu | ............................... | 585/512 |
| 5,227,561 | A | * | 7/1993 | Drent | ............................. | 585/514 |
| 6,667,269 | B2 | | 12/2003 | Olivier-Bourbigou et al. | | |

FOREIGN PATENT DOCUMENTS

| DE | 199 15 904 | 10/2000 |
| EP | 0 143 703 | 6/1985 |
| EP | 1 136 124 | 9/2001 |
| FR | 2 724 650 | 3/1996 |
| GB | 601202 | 4/1948 |
| JP | 2001-259429 | 9/2001 |
| RU | 2 100 333 | 12/1997 |
| WO | 2005/037750 | 4/2005 |

OTHER PUBLICATIONS

Wu et al (Organometallics, 1987, 6(11), 2386-91).*
RajanBabu et al (J.Org.Chem., 2003, 68, 8431-8446).*
Ho et al (Angew.Chem.Int.Ed., 2007, 46, 782-785).*
Ho, C.Y., et al., "Catalytic Intermolecular Tail-to-Tail Hydroalkenylation of Styrenes with α Olefins: Regioselective Migratory Insertion Controlled by a Nickel/N-Heterocyclic Carbene", Angew. Chem. Int. Ed., 2010, 49, pp. 9182-9186.

* cited by examiner

*Primary Examiner* — Sudhakar Katakam
(74) *Attorney, Agent, or Firm* — Ping Wang; Andrews Kurth, LLP

(57) ABSTRACT

Disclosed is a process for preparing terminal 1,1-disubstituted alkenes and is to compounds prepared therewith.

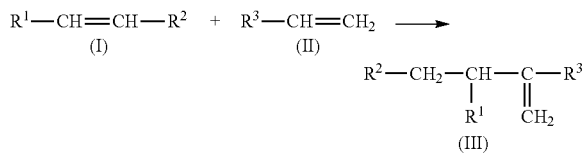

17 Claims, No Drawings

TERMINAL 1,1-DISUBSTITUTED ALKENES, METHOD OF MAKING AND USING THEREOF

FIELD

The present application is in the field of organic synthesis chemistry, in particular, is directed to a process for preparing terminal 1,1-disubstituted alkenes.

BACKGROUND

Synthesis of new alkenes is one of the most important aspects in organic synthesis chemistry. Alkenes may serve as primary starting point for preparations of various materials via subsequent transformations, such as Ziegler-Natta polymerization, Wacker oxidation, and hydroformylation.

Today's major obstacle to reveal the full potential of these indispensible transformations may probably come from the cost of starting materials and their preparation. Most of the alkenes employed in above systems are monosubstituted alkenes, such as α-olefins and styrenes, which are produced in metric megatons amount every year at a low cost. Higher substituted olefins are much less available and relatively costly or indirect syntheses are required. As a result, there are huge demands to develop methodologies that lead to higher substituted alkenes.

SUMMARY

In one aspect, the present application is directed to a process for preparing a compound of formula (III) with a compound of formula (I) and a compound of formula (II) in the presence of a transition metal catalyst or a precursor thereof,

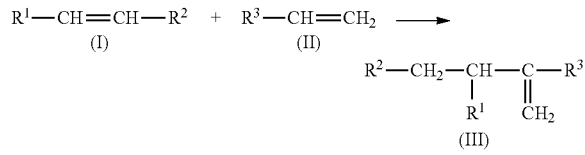

wherein, $R^1$ is optionally substituted aryl, $R^2$ is hydrogen or optionally substituted alkyl, or $R^2$ is alkylene chain with the other end of the alkylene chain being connected to $R^1$, and $R^3$ is optionally substituted aryl or optionally substituted alkyl.

In another aspect, the present application is directed to a compound of formula (III)

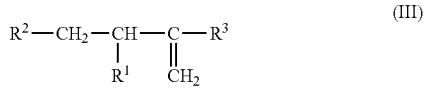

wherein, $R^1$ is optionally substituted aryl, $R^2$ is hydrogen or optionally substituted alkyl, or $R^2$ is alkylene chain with the other end of the alkylene chain being connected to $R^1$, and $R^3$ is optionally substituted aryl or optionally substituted alkyl.

DETAILED DESCRIPTION

Definitions

In the following description, certain specific details are included to facilitate a thorough understanding of various disclosed embodiments. One skilled in the relevant art, however, will recognize that embodiments may be practiced without one or more of these specific details, or with other methods, components, materials, etc.

Unless the context requires otherwise, throughout the specification and claims which follow, the word "comprise" and variations thereof, such as, "comprises" and "comprising" are to be construed in an open, inclusive sense, which is as "including, but not limited to".

Reference throughout this specification to "one embodiment", or "an embodiment", or "in another embodiment", or "some embodiments", or "in some embodiments" means that a particular referent feature, structure, or characteristic described in connection with the embodiment is included in at least one embodiment. Thus, the appearance of the phrases "in one embodiment", or "in an embodiment", or "in another embodiment", or "in some embodiments" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a", "an", and "the" include plural referents unless the content clearly dictates otherwise. In the present application, the use of "or" means "and/or" unless stated otherwise.

Certain chemical groups named herein are preceded by a shorthand notation indicating the total number of carbon atoms that are to be found in the indicated chemical group. For example, $C_7$-$C_{12}$ alkyl describes an alkyl group, as defined below, having a total of 7 to 12 carbon atoms, and $C_4$-$C_{12}$ cycloalkylalkyl describes a cycloalkylalkyl group, as defined below, having a total of 4 to 12 carbon atoms. The total number of carbons in the shorthand notation does not include carbons that may exist in substituents of the group described.

As used herein, "$C_m$ to $C_n$" or "$C_{m\ to\ n}$" in which "m" and "n" are integers refers to the number of carbon atoms in an alkyl, alkenyl or alkynyl group or the number of carbon atoms in the ring of a cycloalkyl or cycloalkenyl group. That is, the alkyl, alkenyl, alkynyl, ring of the cycloalkyl or ring of the cycloalkenyl can contain from "m" to "n", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "m" and "n" are designated with regard to an alkyl, alkenyl, alkynyl, cycloalkyl or cycloalkenyl group, the broadest range described in these definitions is to be assumed.

Accordingly, as used in the specification and appended claims, unless specified to the contrary, the following terms have the meaning indicated:

The term "alkyl" as used herein alone or as part of a group means any unbranched or branched, substituted or unsubstituted, saturated hydrocarbon group. The alkyl moiety, may be branched or straight chain. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from substituted or unsubstituted cycloalkyl, substituted or unsubstituted cylcloalkenyl, substituted or unsubstituted aryl, substituted or unsubstituted heteroaryl, substituted or unsubstituted heteroaryloxy, heterocyclyl, heterocyclooxy, heteroalicyclyl, hydroxy, substituted or unsubstituted alkoxy, substituted or unsubstituted aryloxy, acyl, thiol, substituted or unsubstituted thioalkoxy, alkylthio, arylthio, cyano, halo, carbonyl, thiocarbonyl, acylalkyl, acylamino, acyloxy, aminoacyl, aminoacyloxy, oxyacylamino, keto, thioketo, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and substituted or unsubstituted amino, including mono- and di-substituted amino groups, and the protected derivatives thereof, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

Typical alkyl groups include, but are in no way limited to, methyl, ethyl, propyl, isopropyl, butyl, isobutyl, tertiary butyl, pentyl, hexyl, and the like. Wherever a substituent is described as being "optionally substituted", that substitutent may be substituted with one or more of the above substituents.

The term "alkenyl" as used herein alone or as part of a group refers to a straight or branched hydrocarbon chain group consisting solely of carbon and hydrogen atoms, containing at least one double bond, having from two to twelve carbon atoms, preferably two to eight carbon atoms and which is attached to the rest of the molecule by a single bond, e.g., ethenyl, propenyl, butenyl, pentenyl, penta-1,4-dienyl, and the like.

The term "alkynyl" as used herein alone or as part of a group refers to a straight or branched hydrocarbon chain group consisting solely of carbon and hydrogen atoms, containing at least one triple bond, having from two to twelve carbon atoms, preferably two to eight carbon atoms and which is attached to the rest of the molecule by a single bond, e.g., ethynyl, propynyl, butynyl, pentynyl, hexynyl, and the like.

The term "alkylene" or "alkylene chain" as used herein alone or as part of a group refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain.

The term "alkenylene" or "alkenylene chain" as used herein alone or as part of a group refers to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

The term "alkynylene" or "alkynylene chain" as used herein alone or as part of a group refers to a straight or branched divalent hydrocarbon chain linking the rest of the molecule to a radical group, consisting solely of carbon and hydrogen, containing at least one triple bond and having from two to twelve carbon atoms, e.g., propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain.

The term "cycloalkyl" as used herein alone or as part of a group refers to a completely saturated (no double bonds) mono- or multi-cyclic hydrocarbon ring system. When composed of two or more rings, the rings may be joined together in a fused, bridged or spiro-connected fashion. Cycloalkyl groups of the present application may range from $C_3$ to $C_{10}$. In other embodiments, it may range from $C_3$ to $C_6$. A cycloalkyl group may be unsubstituted or substituted. Typical cycloalkyl groups include, but are not limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated.

The term "cycloalkenyl" as used herein alone or as part of a group refers to a cycloalkyl group that contains one or more double bonds in the ring although, if there is more than one, they cannot form a fully delocalized pi-electron system in the ring (otherwise the group would be "aryl", as defined herein). When composed of two or more rings, the rings may be connected together in a fused, bridged or spiro-connected fashion. A cycloalkenyl group of the present application may be unsubstituted or substituted. When substituted, the substituent(s) may be an alkyl or selected from the groups disclosed above with regard to alkyl group substitution unless otherwise indicated.

The term "cycloalkynyl" as used herein alone or as part of a group refers to a cycloalkyl group that contains one or more triple bonds in the ring. When composed of two or more rings, the rings may be joined together in a fused, bridged or spiro-connected fashion. A cycloalkynyl group of the present application may be unsubstituted or substituted. When substituted, the substituent(s) may be an alkyl or selected from the groups disclosed above with regard to alkyl group substitution unless otherwise indicated.

The term "carbonyl" as used herein alone or as part of a group refers to the group —(C═O).

The term "alkoxy" as used herein alone or as part of a group refers to any unbranched, or branched, substituted or unsubstituted, saturated or unsaturated ether, with $C_1$-$C_6$ unbranched, saturated, unsubstituted ethers being preferred, with methoxy and ethoxy being preferred.

The term "alkylamino" as used herein alone or as part of a group refers to the group —NH-alkyl.

The term "dialkylamino" herein alone or as part of a group refers to the group —N(alkyl)$_2$, where the alkyl groups may be the same or different.

The term "alkylcarbonyl" as used herein alone or as part of a group refers to an alkyl group bonded through a carbonyl group.

The term "alkoxycarbonyl" as used herein alone or as part of a group refers to an alkoxy group bonded through a carbonyl group.

The term "alkylaminocarbonyl" as used herein alone or as part of a group refers to an alkylamino group bonded through a carbonyl group.

The term "dialkylaminocarbonyl" as used herein alone or as part of a group refers to a dialkylamino group bonded through a carbonyl group.

The term "cycloalkoxy" as used herein alone or as part of a group refers to a cycloalkyl group, as defined above, covalently bonded to the parent molecule through an —O— linkage.

The term "halo" or "halogen" as used herein alone or as part of a group refers to bromo, chloro, fluoro or iodo.

The term "haloalkyl" as used herein alone or as part of a group refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

The term "trihaloalkyl" as used herein alone or as part of a group refers to an alkyl radical, as defined above, which is substituted by three halo radicals, as defined above, e.g., trifluoromethyl. The alkyl part of the trihaloalkyl radical may be optionally substituted as defined above for an alkyl group.

The term "haloalkoxy" as used herein alone or as part of a group refers to an alkoxy radical, as defined above, that is substituted by one or more halo radicals, as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like. The alkoxy part of the haloalkoxy radical may be optionally substituted as defined above for an alkoxy group.

The term "trihaloalkoxy" as used herein alone or as part of a group refers to an alkoxy group, as defined above, which is substituted by three halo radicals, as defined above. The alkoxy part of the trihaloalkoxy group may be optionally substituted as defined above for an alkoxy group.

The term "heterocyclyl" as used herein alone or as part of a group is intended to mean three-, four-, five-, six-, seven-, and eight- or more membered rings wherein carbon atoms together with from 1 to 3 heteroatoms constitute the ring. A heterocyclyl can optionally contain one or more unsaturated bonds situated in such a way, however, that an aromatic pi-electron system does not arise. The heteroatoms are independently selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclyl rings can optionally be fused ring systems containing two or more rings wherein at least one atom is shared between two or more rings to form bicyclic or tricyclic structures. In some embodiments, such fused ring systems are formed by a bridging moiety between two atoms of a heterocyclyl.

Heterocyclyl rings can optionally also be fused to aryl rings, such that the definition includes bicyclic structures. Typically such fused heterocyclyl groups share one bond with an optionally substituted benzene ring. Examples of benzo-fused heterocyclyl groups include, but are not limited to, benzimidazolidinone, tetrahydroquinoline, and methylenedioxybenzene ring structures.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidine, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane, and an azabicyclo system such as azabicyclo[3.2.1]octyl (tropane). Binding to the heterocycle can be at the position of a heteroatom or via a carbon atom of the heterocycle, or, for benzo-fused derivatives, via a carbon of the benzenoid ring.

The term "aromatic" as used herein refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups.

The term "carbocyclic" as used herein, refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" as used herein, refers to an aromatic group which contains at least one heterocyclic ring.

The term "aryl" as used herein alone or as part of a group is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl.

The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "arylalkyl" or "aralkyl" as used herein alone or as part of a group which are used synonymously and interchangeably refers to an aryl group covalently bonded to an alkyl group, as defined herein. A "phenylalkyl" is a species of an aralkyl group, and refers to a phenyl ring covalently bonded to an alkyl group as defined herein. Examples of phenylalkyl groups include, but are not limited to, benzyl, 2-phenylethyl, 1-phenylpropyl, 4-phenylhexyl, 3-phenylamyl and 3-phenyl-2-methylpropyl. Presently preferred phenylalkyl groups are those wherein the phenyl group is covalently bonded to one of the presently preferred alkyl groups. A phenyl alkyl group of the present application may be unsubstituted or substituted. Examples of substituted phenylalkyl groups include, but are not limited to, 2-phenyl-1-chloroethyl, 2-(4-methoxyphenyl)ethyl, 4-(2,6-dihydroxyphenyl)hexyl, 2-(5-cyano-3-methoxyphenyl)pentyl, 3-(2,6-dimethylphenyl)propyl, 4-chloro-3-aminobenzyl, 6-(4-methoxyphenyl)-3-carboxy(n-hexyl), 5-(4-aminomethylphenyl)-3-(aminomethyl)pentyl and 5-phenyl-3-oxo-pent-1-yl.

The term "heteroaryl" as used herein alone or as part of a group is intended to mean a heterocyclic aromatic group where one or more carbon atoms in an aromatic ring have been replaced with one or more heteroatoms selected from the group comprising nitrogen, sulfur, and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one cycloalkyl ring share at least one chemical bond.

The term "heteroaryl" is understood to relate to aromatic, $C_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, for example, connected via one of the ring-forming carbon atoms. Heteroaryl groups can carry one or more substituents, selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, heteroaryl groups can be five- and six-membered aromatic heterocyclic systems carrying 0, 1, or 2 substituents, which can be the same as or different from one another, selected from the list above.

Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The term "phenyl" as used herein alone or as part of a group refers to a six-membered aryl group. A phenyl group may be unsubstituted or substituted. When substituted the substituent(s) is(are) one or more, preferably one or two, group(s) independently selected from the group consisting of halogen, hydroxy, protected hydroxy, cyano, nitro, alkyl, alkoxy, acyl, acyloxy, carboxy, protected carboxy, carboxymethyl, protected carboxymethyl, hydroxymethyl, protected hydroxymethyl, —NRR', carboxamide, protected carboxamide, N-alkylcarboxamide, protected N-alkylcarboxamide, N,N-dialkylcarboxamide, trifluoromethyl, N-alkylsulfonylamino, N-(phenylsulfonyl)amino and phenyl (resulting in the formation of a biphenyl group).

Examples of substituted phenyl groups include, but are not limited to, 2-, 3- or 4-chlorophenyl, 2,6-dichlorophenyl, 2,5-dichlorophenyl, 3,4-dichlorophenyl, 2-, 3- or 4-bromophenyl, 3,4-dibromophenyl, 3-chloro-4-fluorophenyl, 2-, 3- or 4-fluorophenyl, 2-, 3- or 4-hydroxyphenyl, 2,4-dihydroxyphenyl, the protected-hydroxy derivatives thereof, 2-, 3- or 4-nitrophenyl; 2-, 3- or 4-cyanophenyl, 2-, 3- or 4-methylphenyl, 2,4-dimethylphenyl, 2-, 3- or 4-(iso-propyl)phenyl, 2-, 3- or 4-ethylphenyl, 2-, 3- or 4-(n-propyl)phenyl, 2,6-dimethoxyphenyl, 2-, 3- or 4-methoxyphenyl, 2-, 3- or 4-ethoxyphenyl, 2-, 3- or 4-(isopropoxy)phenyl, 2-, 3- or 4-(t-butoxy)phenyl, 3-ethoxy-4-methoxyphenyl, 2-, 3- or 4-trifluoromethylphenyl, 2-, 3- or 4-carboxyphenyl or 2,4-di(protected carboxy)phenyl, 2-, 3-, or 4-(protected hydroxymethyl)phenyl or 3,4-di(hydroxymethyl)phenyl, 2-, 3- or 4-(aminomethyl)phenyl or 2,4-(protected aminomethyl)phenyl, and 2-, 3- or 4-(N-(methylsulfonylamino))phenyl.

The term "phenylalkoxy" as used herein alone or as part of a group refers to a "phenylalkyl-O-" group with "phenyl" and "alkyl" as defined herein. A phenylalkoxy group of the present application may be substituted or unsubstituted on the phenyl ring, in the alkyl group or both. Examples of phenylalkoxy groups include, but are not limited to, 2-(4-hydroxyphenyl)ethoxy, 4-(4-methoxyphenyl)butoxy, (2R)-3-phenyl-2-amino-propoxy, (2S)-3-phenyl-2-amino-propoxy, 2-indanoxy, 6-phenyl-1-hexanoxy, cinnamyloxy, 2-phenyl-1-propoxy and 2,2-dimethyl-3-phenyl-1-propoxy.

The term "alkylthio" as used herein alone or as part of a group refers to an "alkyl-S-" group, with alkyl as defined above. Examples of alkylthio group include, but are not limited to, methylthio, ethylthio, n-propylthio, isopropylthio, n-butylthio and t-butylthio.

The term "alkylsulfinyl" as used herein alone or as part of a group refers to an "alkyl-SO-" group, with alkyl as defined above. Examples of alkylsulfinyl groups include, but are not limited to, methylsulfinyl, ethylsulfinyl, n-propylsulfinyl, isopropylsulfinyl, n-butylsulfinyl and sec-butylsulfinyl.

The term "alkylsulfonyl" as used herein alone or as part of a group refers to an "alkyl-$SO_2$-" group. Examples of alkylsulfonyl groups include, but are not limited to, methylsulfonyl, ethylsulfonyl, n-propylsulfonyl, isopropylsulfonyl, n-butylsulfonyl, and t-butylsulfonyl.

The terms "phenylthio", "phenylsulfinyl", and "phenylsulfonyl" as used herein alone or as part of a group refer to a "phenyl-S-", "phenyl-SO-", and "phenyl-$SO_2$-" group, phenyl as defined herein.

The term "amine" as used herein refers to a compound that comprises an amino group. The term "amino" as used herein alone or as part of a group refers to the —$NH_2$ radical.

The term "cyano" as used herein alone or as part of a group refers to the —CN radical.

The term "hydroxy" as used herein alone or as part of a group refers to the —OH radical.

The term "imine" as used herein refers to a compound that comprises an imino group. The term "imino" as used herein alone or as part of a group refers to the =NH substituent.

The term "nitro" as used herein alone or as part of a group refers to the —$NO_2$ radical.

The term "oxo" as used herein alone or as part of a group refers to the =O substituent.

The term "thioxo" as used herein alone or as part of a group refers to the substituent.

The term "trifluoromethyl" as used herein alone or as part of a group refers to the —$CF_3$ radical.

The term "optional" or "optionally" as used herein means that the subsequently described event of circumstances may or may not occur, and that the description includes instances where said event or circumstance occurs and instances in which it does not.

Unless otherwise indicated, when a substituent is deemed to be "optionally substituted", it is meant that the substituent is a group that may be substituted with one or more group(s) individually and independently selected from morpholinoalkanoate, cycloalkyl, aryl, heteroaryl, heterocyclyl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof.

For example, "optionally substituted aryl" means that the aryl radical may or may not be substituted and that the description includes both substituted aryl radicals and aryl radicals having no substitution.

The term "transition metal" as used herein refers to any element in the d-block of the periodic table of the elements. This corresponds to groups 3 (IIIB) to 12 (IIB) on the periodic table.

The term "ligand" in chemistry generally refers to an atom, ion, or molecule that bonds to a central metal, generally involving formal donation of one or more of its electrons. The metal-ligand bonding ranges from covalent to more ionic.

The term "carbene(s)" as used herein refers to an organic molecule containing a carbon atom with six valence electrons and having the general formula RR'C.

In one aspect, the present application is directed to a process for preparing a compound of formula (III) with a compound of formula (I) and a compound of formula (II) in the presence of a transition metal catalyst or a precursor thereof,

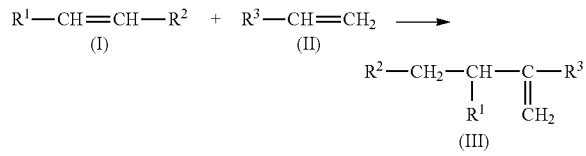

wherein, $R^1$ is optionally substituted aryl, $R^2$ is hydrogen or optionally substituted alkyl, or $R^2$ is alkylene chain with the other end of the alkylene chain being connected to $R^1$, and $R^3$ is optionally substituted aryl or optionally substituted alkyl.

In some embodiments of the present application, $R^1$ is optionally substituted phenyl, naphthalenyl, phenanthrenyl, anthracenyl, tetralinyl, fluorenyl, indenyl, or indanyl.

In some embodiments of the present application, the compound of formula (I) is selected from the group consisting of styrene, beta-methylstyrene, benzocyclohexene, indene, heteroaromatic alkene and substituted derivatives.

In some embodiments of the present application, $R^2$ is optionally substituted alkyl, and the relative configuration of the olefin stereochemistry of the compound of formula (I) may be cis-, trans- or mixture thereof.

In some embodiments of the present application, $R^3$ is optionally substituted phenyl, naphthalenyl, phenanthrenyl, anthracenyl, tetralinyl, fluorenyl, indenyl, or indanyl.

In some embodiments of the present application, $R^3$ is optionally substituted alkyl.

In some embodiments of the present application, the compound of formula (II) is selected from the group consisting of straight chain monoenes such as 1-hexene or 1-octene, branched chain monoenes such as vinylcyclohexane or 4-methyl-1-butene, aromatic alkenes such as styrene or allylbenzene, and their substituted derivatives.

The transition metal catalyst of the present invention may include any catalytic transition metal and/or catalyst precursor as it is introduced into the reaction vessel and which may be, if needed, converted in situ into active form, as well as the active form of the catalyst which participates in the reaction. In some embodiments of the present application, the transition metal is selected from Groups 3 to 12.

Exemplary transition metal that can be used in the present application includes, but is not limited to, Scandium (Sc), Titanium (Ti), Vanadium (V), Chromium (Cr), Manganese (Mn), Iron (Fe), Cobalt (Co), Nickel (Ni), Copper (Cu), Zinc (Zn), Yttrium (Y), Zirconium (Zr), Niobium (Nb), Molybdenum (Mo), Technetium (Tc), Ruthenium (Ru), Rhodium (Rh), Palladium (Pd), Silver (Ag), Cadmium (Cd), Hafnium (Hf), Tantalum (Ta), Tungsten (W), Rhenium (Re), Osmium (Os), Iridium (Ir), Platinum (Pt), Gold (Au), Mercury (Hg), Rutherfordium (Rf), Dubnium (Db), Seaborgium (Sg), Bohrium (Bh), Hassium (Hs), Meitnerium (Mt), Darmstadtium (Ds), Roentgenium (Rg), and Ununbium (Uub).

In some embodiments of the present application, the transition metal is selected from Group 10.

In some embodiments of the present application, the transition metal is selected from the group consisting of Nickel (Ni), Palladium (Pd) and Platinum (Pt). In some embodiments of the present application, the transition metal is Nickel (Ni).

In some embodiments of the present application, a ligand on the transition metal catalyst is selected from the group consisting of carbenes, heterocyclic carbenes, biscarbenes, bisheterocyclic carbenes, phosphines, amines, imines, arsines, and their hybrids, combinations, and derivatives.

Exemplary amines that can be used in the present application include, but are not limited to, aliphatic amines, and aromatic amines. Exemplary aliphatic amines that can be used in the present application include, but are not limited to, primary amines, secondary amines, and tertiary amines. Exemplary aliphatic amines that can be used in the present application include, but are not limited to, methylamine, ethanolamine, dimethylamine, methylethanolamine, trimethylamine, aziridine, piperidine, N-methylpiperidine, and the like. Exemplary aromatic amines that can be used in the present application include, but are not limited to, aniline, o-toluidine, 2,4,6-trimethylaniline, anisidine, 3-trifluoromethylaniline, and the like.

In some embodiments of the present application, the ligand or metal bears a weakly or non-nucleophilic stabilizing ion, including but not limited to halogen, sulfonates, and phosphonates.

The ligand can be added to the reaction mixture in the form of a metal complex, or added as separate reagent relative to the addition of the metal. The ligand, if chiral, can be provided as a racemic mixture or a purified stereoisomer.

In some embodiments of the present application, the ligand is IPr (IPr=1,3-bis(2,6-di-isopropylphenyl)imidazol-2-ylidene; CAS: 244187-81-3). In some embodiments of the present application, the transition metal catalyst is [IPr—Ni—H]OTf or its dimer, trimer or higher order oligomers (IPr=1,3-bis(2,6-di-isopropylphenyl)imidazol-2-ylidene; CAS: 244187-81-3).

In some embodiments of the present application, the transition metal catalyst is provided in the reaction in a catalytic amount. In certain embodiments, that amount is in the range of <5 mol %, with respect to the limiting reagent, which may be either the compound of formula (I) or the compound of formula (II), depending upon which reagent is in stoichiometric excess.

In some embodiments of the present application, the reaction can be carried out optionally with a solvent. The solvent is selected from the group consisting of aromatic hydrocarbons, aliphatic hydrocarbons, alicyclic hydrocarbons, halohydrocarbons, alcohols, ethers, esters, ketones, nitriles and diol derivatives.

Exemplary aromatic hydrocarbons that can be used in the present application include, but are not limited to, benzene, toluene, xylene, and the like. Exemplary aliphatic hydrocarbons that can be used in the present application include, but are not limited to, pentane, hexane, heptane, octane, and the like. Exemplary alicyclic hydrocarbons that can be used in the present application include, but are not limited to, cyclohexane, cyclohexanone, methylcyclohexanone, and the like. Exemplary alcohols that can be used in the present application include, but are not limited to, methanol, ethanol, isopropanol, and the like. Exemplary ethers that can be used in the present application include, but are not limited to, diethyl ether, methyl ethyl ether, propyl ether, propylene oxide, and the like. Exemplary esters that can be used in the present application include, but are not limited to, methyl formate, ethyl formate, butyl formate, pentyl formate, methyl acetate, ethyl acetate, propyl acetate, benzyl phenylacetate, and the like. Exemplary ketones that can be used in the present application include, but are not limited to, acetone, methylbutanone, methyl isobutyl ketone, and the like. Exemplary nitriles that can be used in the present application include, but are not limited to, acetonitrile, propionitrile, acrylonitrile, and the like. Exemplary diol derivatives that can be used in the present application include, but are not limited to, ethylene glycol monomethyl ether, ethylene glycol monoethyl ether, ethylene glycol monobutyl ether, and the like.

In some embodiments of the present application, the solvent is an aromatic hydrocarbon. In some embodiments of the present application, the solvent is selected from the group consisting of benzene, toluene and xylene.

Alternatively, the reaction can be carried out in the alkene substrates themselves (neat condition). Ionic liquid, such as imidazolium salts, can be also used as reaction medium.

In some embodiments of the present application, the process may be carried out optionally in a buffer to minimize the problems related to isomerization, oligomerization and polymerization. Examples of the buffer which can be used in the present application include but not limited to ammonium salt, phosphorous buffer, carbonates.

In another aspect, the present application is directed to a compound of formula (III)

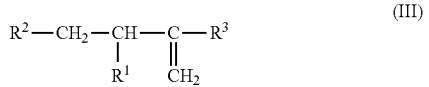

$R^1$ is optionally substituted aryl,
$R^2$ is hydrogen or optionally substituted alkyl, or $R^2$ is alkylene chain with the other end of the alkylene chain being connected to $R^1$, and
$R^3$ is optionally substituted aryl or optionally substituted alkyl.

In some embodiments of the present application, $R^1$ is optionally substituted phenyl, naphthalenyl, phenanthrenyl, anthracenyl, tetralinyl, fluorenyl, indenyl, or indanyl.

In some embodiments of the present application, $R^3$ is optionally substituted phenyl, naphthalenyl, phenanthrenyl, anthracenyl, tetralinyl, fluorenyl, indenyl, or indanyl.

In some embodiments of the present application, $R^3$ is optionally substituted alkyl.

EXAMPLES

The reaction is highly oxygen and moisture sensitive, the substrates shall be dried and degassed before use (normally over $CaH_2$, except for 1-(chloromethyl)-4-vinylbenzene, which was dried over powdered $CaCl_2$ overnight; and 2-vinyl naphthalene, which is a solid and was used directly). Unless otherwise indicated, all reactions were performed under an oxygen-free atmosphere of nitrogen or argon with rigid exclusion of moisture from reagents and glassware. Bis(cyclooctadienyl)nickel(0) (Ni(cod)2) was purchased from ACROS or IL, stored under nitrogen atmosphere and used without further purification. IPr, TESOTf and $NEt_3$ were purchased from Aldrich or Strem. Alkenes were filtered through a short plug of silica gel and dried before use to remove possible stabilizer. Toluene was distilled over sodium before use.

Analytical thin layer chromatography (TLC) was performed using EM Science silica gel 60 F254 plates. The developed chromatogram was analyzed by UV lamp (254 nm), ethanolic phosphomolybdic acid (PMA) or potassium permanganate ($KMnO_4$). Liquid chromatography was performed using a forced flow (flash chromatography) of the indicated solvent system on Silica Gel (230-400 mesh). $^1H$ and $^{13}C$ NMR spectra were recorded on Bruker 400 MHz or 300 MHz spectrometers in $CDCl_3$. Chemical shifts in $^1H$ NMR spectra are reported in ppm on the δ scale from an internal standard of residual chloroform (7.27 ppm). Data are reported as follows: chemical shift, multiplicity (s=singlet, d=doublet, t=triplet, q=quartet, m=multiplet, br=broad), coupling constant in hertz (Hz), and integration. Chemical shifts of $^{13}C$ NMR spectra are reported in ppm from the central peak of $CDCl_3$ (77.16 ppm) on the δ scale.

Preliminary Screening and In Situ Generation of [IPr—Ni—H]OTf Catalyst

The catalyst with a general formula of [NHC—Ni—H]X (wherein X can be any halogen, sulfonates or other non-nucleophilic ions), [IPr—Ni—H]OTf as an example in this case, can be generated according to but not limited to the following literature procedure with modifications: "Highly Selective Coupling of Alkenes and Aldehydes Catalyzed by [Ni(NHC){P(OPh)₃}]: Synergy between a Strong σ Donor and a Strong π Acceptor" Chun-Yu Ho, Timothy F. Jamison, *Angew. Chem. Int. Ed.* 2007, 46, 782.

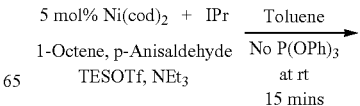

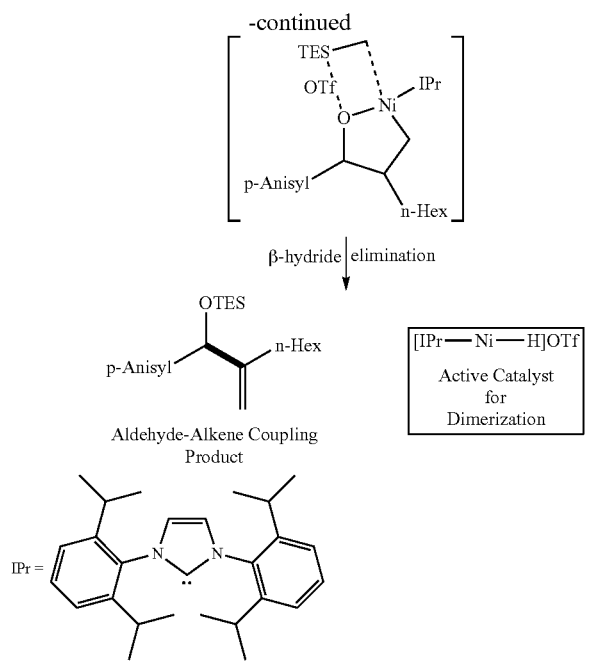

The [NHC—Ni—H]X species can be also generated by other methods, include but not limited to mixing a Ni source with 1) an imidazolium salt or an ionic liquid in general; or 2) alkyl, aryl, benzyl, vinyl, alkenyl or alkynyl X; or 3) a hydride or hydrogen source in general, optionally with the use of activators and buffers, this include but not limited to Lewis acidic additives, protic acid and or nucleophiles; or 4) other common organometallic transfromations and manipulations techniques, such as hydride addition or elimination steps.

For example:

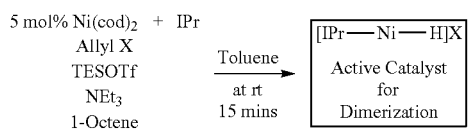

Experimental results suggested that the coupling reactions are sensitive to the carbene catalyst structures, the counter ion used and possibly generation methods.

Solvent screening revealed that THF can also be used as solvent in place of toluene for the styrene-octene cross-dimerization, giving similar yield and selectivity.

1,3-bis(2,6-di-isopropylphenyl)imidazol-2-ylidene (IPr) (0.05 mmol, 5 mol %) and Ni(cod)$_2$ (0.05 mmol, 5 mol %) were added to an oven-dried test tube equipped with a stir bar in glove box. The tube was sealed with a septum, brought out of the glove box, and connected to a nitrogen line. The catalyst mixture was dissolved in degassed toluene (2 mL) under nitrogen and stirred at room temperature for 1 hour. The 1-octene (10 mol %), triethylamine (0.3 mmol), p-anisaldehyde (0.05 mmol, 5 mol %), triethylsilyltriflate (0.1 mmol, 10 mol %) were then added sequentially to the reaction mixture, and the mixture was stirred for 15 mins at rt.

General Procedure for Cross-Dimerization of Vinyl Arenes with α-Olefins:

The α-olefin and vinyl arene (3 mmol, 300 mol % and 1 mmol, 100 mol %, respectively) were added to the [IPr—Ni—H]OTf catalyst mixture together at room temperature. (The α-olefin can also be added during the catalyst generation, the self-dimerization of α-olefin, especially branched chain olefin, is much slower than the cross-dimerization. When a solid substrate was used, the substrate was added as a stock solution in toluene). The mixture was stirred 24 h at room temperature (23° C.). Then the mixture was diluted with n-Hexane (4 mL) and was allowed to stir 30 mins in open air at room temperature. The mixture was then filtered through a short plug of silica gel and rinsed with 20% ethyl acetate/hexane (75 mL). The solvent was removed under reduced pressure, and purification via flash chromatography on silica gel (hexane, unless otherwise indicated) afforded the coupling product.

General Procedure for Self-Dimerization of Vinyl Arene:

The general dimerization procedure was followed, except that the α-olefin substrate was replaced by 1 mmol of vinyl arene after the catalyst generation.

Following the above general procedures, the following compounds are synthesized from the corresponding starting materials and the characterization data thereof are provided.

Example 1

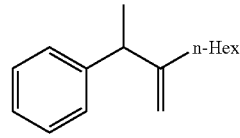

$^1$H NMR (400 MHz, CDCl$_3$) δ: 7.28-7.17 (m, 5H), 4.92 (s, 1H), 4.88 (s, 1H), 3.39 (q, 1H, J=7.1 Hz), 1.93-1.83 (m, 2H), 1.36 (d, 3H, J=7.1 Hz), 1.33-1.21 (m, 8H), 0.85 (t, 3H, J=6.9 Hz).

$^{13}$C NMR (100 MHz, CDCl$_3$) δ: 153.5, 145.7, 128.4, 127.7, 126.1, 108.6, 45.4, 35.2, 31.9, 29.2, 28.1, 22.8, 20.9, 14.2.

HRMS-EI (m/z): [M]$^+$ calcd for C$_{16}$H$_{24}$, 216.1873. found, 216.1879.

Example 2

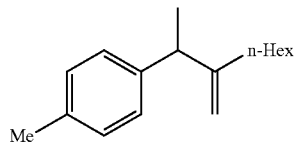

$^1$H NMR (300 MHz, CDCl$_3$) δ: 7.09 (m, 4H), 4.91 (s, 1H), 4.87 (s, 1H), 3.36 (q, 1H, J=7.1 Hz), 2.32 (s, 3H), 1.93-1.77 (m, 2H), 1.38-1.21 (m, 8H), 1.34 (d, 3H, J=7.1 Hz), 0.85 (t, 3H, J=6.9 Hz).

$^{13}$C NMR (75 MHz, CDCl$_3$) δ: 153.7, 142.7, 135.6, 129.1, 127.5, 108.4, 44.9, 35.2, 31.9, 29.2, 28.0, 22.8, 21.2, 21.0, 14.2.

HRMS-EI (m/z): [M]$^+$ calcd for C$_{17}$H$_{26}$, 230.2029. found, 230.20285.

Example 3

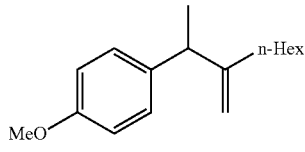

purified by 3% EA/Hex $^1$H NMR (400 MHz, CDCl$_3$) δ: 7.11 (d, 2H, J=8.7 Hz), 6.82 (d, 2H, J=8.7 Hz), 4.90 (s, 1H), 4.85 (s, 1H), 3.78 (s, 3H), 3.35 (q, 1H, J=7.1 Hz), 1.94-1.76 (m, 2H), 1.40-1.19 (m, 8H), 1.33 (d, 3H, J=7.1 Hz), 0.85 (t, 3H, J=6.9 Hz).

$^{13}$C NMR (100 MHz, CDCl$_3$) δ: 158.0, 153.8, 137.8, 128.5, 113.7, 108.3, 55.3, 44.5, 35.1, 31.9, 29.2, 28.1, 22.8, 21.0, 14.2.

HRMS-EI (m/z): [M]$^+$ calcd for C$_{17}$H$_{26}$O, 246.1978. found, 246.1986.

Example 4

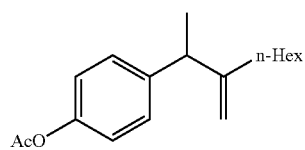

purified by 3% EA/Hex $^1$H NMR (400 MHz, CDCl$_3$) δ: 7.11 (d, 2H, J=8.7 Hz), 6.82 (d, 2H, J=8.7 Hz), 4.90 (s, 1H), 4.85 (s, 1H), 3.35 (q, 1H, J=7.1 Hz), 2.26 (s, 3H), 1.94-1.76 (m, 2H), 1.40-1.19 (m, 8H), 1.33 (d, 3H, J=7.1 Hz), 0.85 (t, 3H, J=6.9 Hz).

$^{13}$C NMR (100 MHz, CDCl$_3$) δ: 169.5, 153.4, 149.2, 143.2, 128.6, 121.3, 108.9, 45.0, 35.1, 31.9, 29.2, 28.1, 22.7, 21.2, 20.8, 14.1.

HRMS-EI (m/z): [M]$^+$ calcd for C$_{18}$H$_{26}$O$_2$, 274.1927. found, 274.1914.

Example 5

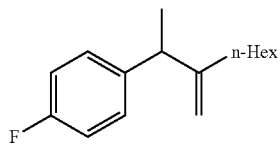

$^1$H NMR (400 MHz, CDCl$_3$) δ: 7.14 (dd, 2H, J=8.7, 5.5 Hz), 6.96 (d, 1H, J=8.7 Hz), 6.96 (d, 1H, J=8.7 Hz), 4.90 (s, 1H), 4.88 (s, 1H), 3.38 (q, 1H, J=7.1 Hz), 1.93-1.76 (m, 2H), 1.46-1.20 (m, 8H), 1.33 (d, 3H, J=7.1 Hz), 0.85 (t, 3H, J=6.9 Hz).

$^{13}$C NMR (100 MHz, CDCl$_3$) δ: 161.5 (d, J=242.0 Hz), 153.3, 141.3, 129.0 (d, J=8.0 Hz), 115.0 (d, J=21.0 Hz), 108.8, 44.7, 35.1, 31.9, 29.2, 28.0, 22.8, 21.0, 14.2.

HRMS-EI (m/z): [M]$^+$ calcd for C$_{16}$H$_{23}$F, 234.1778. found, 234.1788.

Example 6

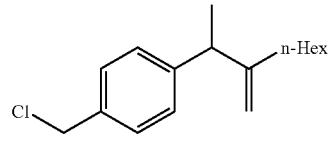

purified by 3% EA/Hex $^1$H NMR (400 MHz, CDCl$_3$) δ: 7.29 (d, 2H, J=8.1 Hz), 7.18 (d, 2H, J=8.1 Hz), 4.91 (s, 1H), 4.89 (s, 1H), 4.57 (s, 2H), 3.39 (q, 1H, J=7.0 Hz), 1.91-1.76 (m, 2H), 1.43-1.18 (m, 8H), 1.34 (d, 3H, J=7.0 Hz), 0.85 (t, 3H, J=6.9 Hz).

$^{13}$C NMR (100 MHz, CDCl$_3$) δ: 153.3, 146.2, 135.4, 128.7, 128.1, 109.0, 46.3, 45.3, 35.2, 31.9, 29.2, 28.1, 22.7, 20.8, 14.2.

HRMS-EI (m/z): [M]$^+$ calcd for C$_{17}$H$_{25}$Cl, 264.1639. found, 264.1638.

Example 7

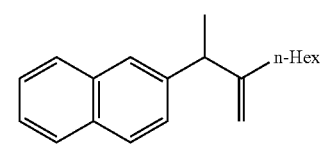

$^1$H NMR (400 MHz, CDCl$_3$) δ: 7.80-7.74 (m, 3H), 7.64 (s, 1H), 7.46-7.39 (m, 2H), 7.33 (dd, 1H, J=8.4, 6.7 Hz), 4.99 (s, 1H), 4.94 (s, 1H), 3.57 (q, 1H, J=7.0 Hz), 1.93-1.85 (m, 2H), 1.44 (d, 3H, J=7.0 Hz), 1.42-1.18 (m, 8H), 0.83 (t, 3H, J=7.0 Hz).

$^{13}$C NMR (100 MHz, CDCl$_3$) δ: 153.3, 143.2, 133.7, 132.4, 128.0, 127.8, 127.7, 126.5, 125.9, 125.8, 125.3, 108.9, 45.5, 35.2, 31.9, 29.2, 28.0, 22.7, 20.8, 14.2.

HRMS-EI (m/z): [M]$^+$ calcd for C$_{20}$H$_{26}$, 266.2029. found, 266.2033.

Example 8

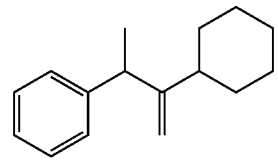 [SMILES: C=C(C1CCCCC1)C(C)c1ccccc1]

$^1$H NMR (400 MHz, CDCl$_3$) δ: 7.28-7.15 (m, 5H), 4.92 (s, 1H), 4.91 (s, 1H), 3.47 (q, 1H, J=7.0 Hz), 1.75-1.58 (m, 6H), 1.34 (d, 3H, J=7.0 Hz), 1.26-1.00 (m, 5H).

$^{13}$C NMR (100 MHz, CDCl$_3$) δ: 159.1, 146.0, 128.3, 127.8, 126.0, 107.3, 44.9, 43.4, 34.1, 33.0, 27.1, 26.9, 26.5, 21.6.

HRMS-EI (m/z): [M]$^+$ calcd for C$_{16}$H$_{22}$, 214.1716. found, 214.1715.

Example 9

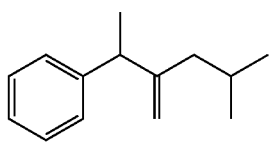

¹H NMR (400 MHz, CDCl₃) δ: 7.29-7.14 (m, 5H), 4.95 (s, 1H), 4.87 (s, 1H), 3.35 (q, 1H, J=7.0 Hz), 1.79-1.71 (m, 3H), 1.35 (d, 3H, J=7.1 Hz), 0.82 (d, 3H, J=6.9 Hz), 0.81 (d, 3H, J=6.9 Hz).

$^{13}$C NMR (100 MHz, CDCl₃) δ: 152.0, 145.7, 128.4, 127.7, 126.2, 110.1, 45.3, 45.0, 26.3, 23.1, 22.2, 21.1.

HRMS-EI (m/z): [M]$^+$ calcd for $C_{14}H_{20}$, 188.1560. found, 188.1559.

Example 10

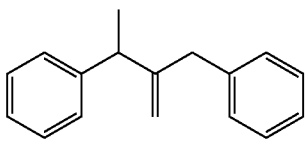 [SMILES: C=C(Cc1ccccc1)C(C)c1ccccc1]

¹H NMR (400 MHz, CDCl₃) δ: 7.30-7.15 (m, 8H), 7.07 (d, 2H, J=6.8 Hz), 5.03 (s, 1H), 4.85 (s, 1H), 3.30 (q, 1H, J=7.0 Hz), 3.27 (d, 1H, J=15.0 Hz), 3.07 (d, 1H, J=15.0 Hz), 1.32 (d, 3H, J=7.0 Hz).

$^{13}$C NMR (100 MHz, CDCl₃) δ: 152.6, 145.4, 140.0, 129.4, 129.3, 128.5, 128.4, 128.3, 127.8, 126.3, 126.1, 111.3, 44.4, 42.2, 21.0.

HRMS-EI (m/z): [M]$^+$ calcd for $C_{17}H_{18}$, 222.1403. found, 222.1415.

Example 11

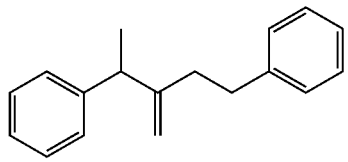 [SMILES: C=C(CCc1ccccc1)C(C)c1ccccc1]

¹H NMR (300 MHz, CDCl₃) δ: 7.30-7.08 (m, 10H), 5.00 (s, 1H), 4.95 (s, 1H), 3.42 (q, 1H, J=6.8 Hz), 2.75-2.59 (m, 2H), 2.28-2.13 (m, 2H), 1.37 (d, 3H, J=6.8 Hz).

$^{13}$C NMR (75 MHz, CDCl₃) δ: 152.7, 145.4, 142.3, 128.5, 128.4, 127.7, 126.3, 125.8, 109.2, 45.7, 36.9, 34.7, 20.8.

HRMS-EI (m/z): [M]$^+$ calcd for $C_{18}H_{20}$, 236.1560. found, 236.1558.

Example 12

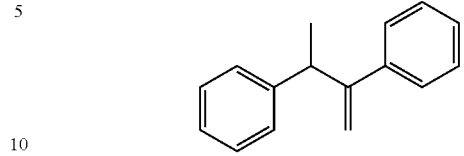

¹H NMR (400 MHz, CDCl₃) δ: 7.30-7.12 (m, 10H), 5.41 (s, 1H), 5.15 (s, 1H), 4.02 (q, 1H, J=7.0 Hz), 1.46 (d, 3H, J=7.0 Hz).

$^{13}$C NMR (100 MHz, CDCl₃) δ: 152.7, 145.2, 142.3, 128.5, 128.2, 127.8, 127.3, 126.8, 126.2, 113.2, 44.3, 21.8.

The compound structure was determined by comparing the literature compound prepared by Wittig reaction of the corresponding ketone spectroscopic data reported. Cui, Xiuhua; Burgess, Kevin. *J. Am. Chem. Soc.* 2003, 125, 14212.

Example 13

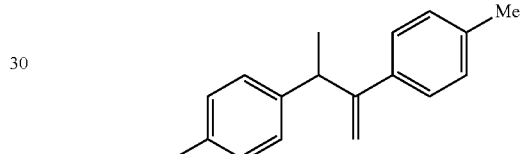

¹H NMR (300 MHz, CDCl₃) δ: 7.20 (d, 2H, J=7.9 Hz), 7.13 (d, 2H, J=8.0 Hz), 7.04 (m, 4H), 5.38 (s, 1H), 5.10 (s, 1H), 3.97 (q, 1H, J=7.1 Hz), 2.27 (s, 6H), 1.43 (d, 3H, J=7.1 Hz).

$^{13}$C NMR (75 MHz, CDCl₃) δ: 152.6, 142.4, 139.5, 136.9, 135.6, 129.2, 128.9, 127.6, 126.7, 112.4, 43.7, 22.1, 21.2, 21.1.

HRMS-EI (m/z): [M]$^+$ calcd for $C_{18}H_{20}$, 236.1560. found, 236.1555.

Example 14

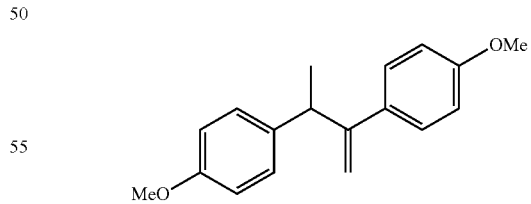

purified by 5% EA/Hex

¹H NMR (400 MHz, CDCl₃) δ: 7.23 (d, 2H, J=8.8 Hz), 7.15 (d, 2H, J=8.8 Hz), 6.79 (d, 2H, J=8.8 Hz), 6.76 (d, 2H, J=8.8 Hz), 5.34 (s, 1H), 5.07 (s, 1H), 3.94 (q, 1H, J=7.0 Hz), 3.75 (s, 3H), 3.74 (s, 3H), 1.42 (d, 3H, J=7.0 Hz).

$^{13}$C NMR (100 MHz, CDCl₃) δ: 158.8, 157.9, 152.2, 137.5, 134.7, 128.6, 127.8, 113.8, 113.5, 111.5, 55.3, 43.4, 22.0.

HRMS-EI (m/z): [M]+ calcd for $C_{18}H_{20}O_2$, 268.1458. found, 268.1467.

Example 15

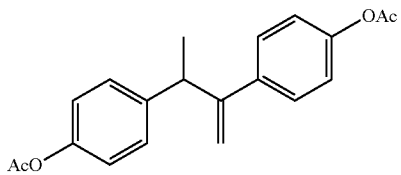 [SMILES: C=C(c1ccc(OC(C)=O)cc1)C(C)c1ccc(OC(C)=O)cc1]

purified by 5% EA/Hex $^1$H NMR (400 MHz, CDCl$_3$) δ: 7.27 (d, 2H, J=8.7 Hz), 7.23 (d, 2H J=8.7 Hz), 6.97 (d, 1H, J=8.7 Hz), 6.95 (d, 2H J=8.7 Hz), 5.39 (s, 1H), 5.15 (s, 1H), 3.98 (q, 1H, J=7.1 Hz), 2.25 (s, 6H), 1.44 (d, 3H, J=7.1 Hz).

$^{13}$C NMR (100 MHz, CDCl$_3$) δ: 169.6, 169.5, 151.5, 149.9, 149.0, 142.4, 139.7, 128.6, 127.7, 121.4, 121.2, 113.6, 43.7, 21.8, 21.2, 21.2.

(m/z): [M]+ calcd $C_{20}H_{20}O_4$, 324.1356. found, 324.1369.

Example 16

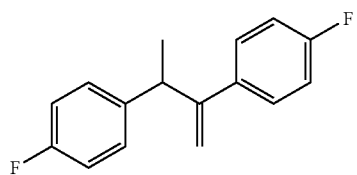 [SMILES: C=C(c1ccc(F)cc1)C(C)c1ccc(F)cc1]

$^1$H NMR (400 MHz, CDCl$_3$) δ: 7.23-7.13 (m, 4H), 6.91 (dd, 4H, J=16.6, 8.6 Hz), 5.35 (s, 1H), 5.15 (s, 1H), 3.95 (q, 1H, J=7.0 Hz), 1.43 (d, 3H, J=7.0 Hz).

$^{13}$C NMR (100 MHz, CDCl$_3$) δ: 162.2 (d, J=245.0 Hz), 161.4 (d, J=245.0 Hz), 151.6, 140.6, 138.1, 129.1 (d, J=7.0 Hz), 128.4 (d, J=7.0 Hz), 115.3 (d, J=21.0 Hz), 115.0 (d, J=21.0 Hz), 113.2, 43.8, 21.8.

HRMS-EI (m/z): [M]+ calcd for $C_{16}H_{14}F_2$, 244.1058. found, 244.1045.

The reaction yields and cross-dimerization:self-dimerization ratios for the above Examples 1-17 are summarized in Table 1 below.

TABLE 1

Summarization of [IPr—Ni—H]OTf catalyzed monoene coupling

| entry[a] | R$^1$ | R$^2$ | Yield (%)[b] | Cross-:Self-Dimerization[c] |
|---|---|---|---|---|
| Cross-Dimerization | | | | |
| 1 | Ph | n-Hex | 80[d] | 69:31 |
|   |    |       | 100    | 90:10 |
|   |    |       | 77[e]  | 38:62 |
|   |    |       | 100[f] | 88:12 |
| 2 | p-MeC$_6$H$_4$ |  | 100 | 90:10 |
| 3 | p-OMeC$_6$H$_4$ |  | 100 | 83:17 |
| 4 | p-OAcC$_6$H$_4$ |  | 95 | 89:11 |
| 5 | p-FC$_6$H$_4$ |  | 92 | 87:13 |
| 6 | p-CH$_2$ClC$_6$H$_4$ |  | 37 (45)[g] | 90:11 |
| 7 | 2-Naphthyl |  | 68 (69)[g] | 94:6 |
| 8 | Ph | Cyclo-Hex | 78 | 50:50 |
|   |    |          | 70[h] | 69:31 |
| 9 |    | CH$_2$ i-Pr | 99 | 89:11 |
| 10 |   | CH$_2$Ph | 74 | 91:9 |
| 11 |   | CH$_2$CH$_2$Ph | 100 | 92:8 |
| Self-Dimerization | | | | |
| 12 |   | Ph | 92 |  |
| 13 |   | p-MeC$_6$H$_4$ | 71 (79)[g] |  |
| 14 |   | p-OMeC$_6$H$_4$ | 95 |  |
| 15 |   | p-OAcC$_6$H$_4$ | 46 (50)[g] |  |
| 16 |   | p-FC$_6$H$_4$ | 42 |  |

[a]No other possible isomers and oligomers were observed in all cases examined. Condition: Alkenes (vinylarene:α-olefin = 1:3 in cross- or 2 mmol of vinylarene in self-dimerization) were added to a solution of in situ generated [IPr—Ni—H]OTf catalyst (5 mol %, 0.05 mmol) in 2 mL toluene at 23° C. under N$_2$, stirred 24 h, products are readily separable by silica gel column chromatography.
[b]Yield based on vinylarene, average of at least two runs and no other regioisomers were observed.
[c]Ratio was determined by $^1$H NMR, self-dimerization refers to vinylarene dimers.
[d]Styrene:1-Octene = 1:1.
[e]Styrene:1-Octene = 3:1, yield based on 1-Octene.
[f]2.5 Fold larger scale.
[g]Vinylarene conversion.
[h]35° C., with slow addition of styrene over 5 hrs.

Example 17

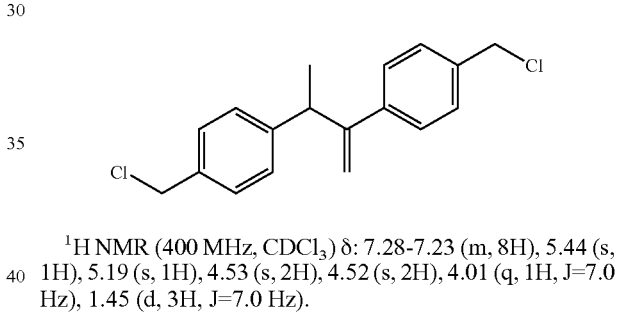

$^1$H NMR (400 MHz, CDCl$_3$) δ: 7.28-7.23 (m, 8H), 5.44 (s, 1H), 5.19 (s, 1H), 4.53 (s, 2H), 4.52 (s, 2H), 4.01 (q, 1H, J=7.0 Hz), 1.45 (d, 3H, J=7.0 Hz).

$^{13}$C NMR (100 MHz, CDCl$_3$) δ: 151.6, 145.4, 142.3, 136.4, 135.4, 128.9, 128.6, 128.1, 127.1, 113.8, 46.3, 46.1, 43.9, 21.8.

HRMS-EI (m/z): [M]+ calcd for $C_{18}H_{18}Cl_2$, 304.0780. found, 304.0793.

Example 18

Indene/1-octene Coupling

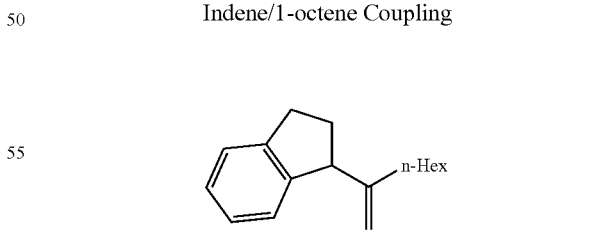

Standard reaction procedure of cross-dimerization was followed, except that the reaction was run at 35° C. and using higher catalyst loading (50%).

Conversion 30%, 27% yield, single product.

$^1$H NMR (400 MHz, CDCl$_3$) δ: 7.24-7.10 (m, 4H), 4.83 (d, 1H, J=1.5 Hz), 4.75 (s, 1H), 3.82 (t, 1H, J=7.8 Hz), 2.99-2.80 (m, 2H), 2.34-2.26 (m, 1H), 2.01-1.89 (m, 3H), 1.27-1.24 (m, 8H), 0.87 (t, 3H).

$^{13}$C NMR (100 MHz, CDCl$_3$) δ: 152.2, 145.9, 144.6, 126.5, 126.2, 124.8, 124.5, 109.9, 52.8, 33.7, 32.4, 32.0, 31.8, 29.4, 28.2, 22.8, 14.3.

HRMS-EI (m/z): [M]$^+$ calcd for C$_{17}$H$_{24}$, 228.1873. found, 228.1868.

Example 19

Anethole/1-octene Coupling

Standard reaction procedure of cross-dimerization was followed, except the reaction was run at 40° C. Only 3 turnovers was observed in 24 hrs (~15% yield, with excellent regioselectivity), and no anethole self-dimerization observed.

$^1$H NMR (400 MHz, CDCl$_3$) δ: 7.10 (d, 2H, J=8.6 Hz), 6.82 (d, 2H, J=8.6 Hz), 4.92 (s, 1H), 4.84 (s, 1H), 3.79 (s, 3H), 3.01 (t, 1H, J=7.5 Hz), 1.87-1.75 (m, 2H), 1.39-1.20 (m, 10H), 0.85 (t, 3H, J=6.9 Hz), 0.82 (t, 3H, J=7.3 Hz).

$^{13}$C NMR (100 MHz, CDCl$_3$) δ: 158.0, 152.8, 136.3, 129.0, 113.6, 108.3, 55.3, 52.8, 35.0, 31.9, 29.2, 27.9, 27.1, 22.8, 14.2, 12.8.

HRMS-EI (m/z): [M]$^+$ calcd for C$_{18}$H$_{28}$O, 260.2140. found, 260.2143. (purified by 3% EA/Hex).

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The above description is for the purpose of teaching the person of ordinary skill in the art how to practice the present application, and it is not intended to detail all those obvious modifications and variations of it which will become apparent to the skilled worker upon reading the description. It is intended, however, that all such obvious modifications and variations be included within the scope of the present application, which is defined by the following claims. The claims are intended to cover the claimed components and steps in any sequence which is effective to meet the objectives there intended, unless the context specifically indicates the contrary.

What is claimed is:

1. A process for preparing a compound of formula (III), comprising:

contacting a compound of formula (I) with a compound of formula (II) in the presence of a transition metal catalyst complex comprising a carbene ligand, thereby forming the compound of formula (III), $$R^1-CH=CH-R^2 \quad (I)$$

$$R^3-CH=CH_2 \quad (II)$$

$$R^2-CH_2-\underset{R^1}{CH}-\underset{\parallel CH_2}{C}-R^3 \quad (III)$$

wherein, R$^1$ is optionally substituted aryl,

R$^2$ is hydrogen or optionally substituted alkyl, or R$^2$ is alkylene chain with the other end of the alkylene chain being connected to R$^1$, and R$^3$ is optionally substituted aryl or optionally substituted alkyl.

2. The process of claim 1, wherein R$^1$ is optionally substituted phenyl, naphthalenyl, phenanthrenyl, anthracenyl, tetralinyl, fluorenyl, indenyl, or indanyl.

3. The process of claim 1, wherein the compound of formula (I) is selected from the group consisting of styrene, beta-methylstyrene, benzocyclohexene, indene, heteroaromatic alkene and substituted derivatives.

4. The process of claim 1, wherein R$^2$ is optionally substituted alkyl, and the relative configuration of the olefin stereochemistry of the compound of formula (I) is cis-, trans- or mixture thereof.

5. The process of claim 1, wherein R$^3$ is optionally substituted phenyl, naphthalenyl, phenanthrenyl, anthracenyl, tetralinyl, fluorenyl, indenyl, or indanyl.

6. The process of claim 1, wherein R$^3$ is optionally substituted alkyl.

7. The process of claim 1, wherein the compound of formula (II) is selected from the group consisting of straight chain monoenes such as 1-hexene or 1-octene, branched chain monoenes such as vinylcyclohexane or 4-methyl-1-butene, aromatic alkenes such as styrene or allylbenzene, and their substituted derivatives.

8. The process of claim 1, wherein the transition metal is selected from Groups 3 to 12.

9. The process of claim 1, wherein the transition metal is selected from Group 10.

10. The process of claim 9, wherein the transition metal is Ni.

11. The process of claim 1, wherein the carbene ligand on the transition metal catalyst is selected from the group consisting of carbenes, heterocyclic carbenes, biscarbenes, bisheterocyclic carbenes, and derivatives thereof.

12. The process of claim 11, wherein the ligand bears a weakly or non-nucleophilic stabilizing ion.

13. The process of claim 11, wherein the ligand is IPr (IPr=1,3-bis(2,6-di-isopropylphenypimidazol-2-ylidene).

14. The process of claim 1, wherein the transition metal catalyst is [IPr—Ni—H]OTf or its dimer, trimer or higher order oligomers (IPr=1,3-bis(2,6-di-isopropylphenypimidazol-2-ylidene), or their optionally substituted allyl or benzyl derivatives.

15. The process of claim 1, wherein the process is carried out in a solvent and the solvent is selected from the group consisting of aromatic hydrocarbons, aliphatic hydrocarbons, alicyclic hydrocarbons, halohydrocarbons, alcohols, ethers, esters, ketones, nitriles and diol derivatives, and ionic liquids such as imidazolium salts.

16. The process of claim 1, wherein the process is carried out in a buffer.

17. The process of claim 1, wherein R$^1$ is aryl.

* * * * *